United States Patent [19]

Harlegard

[11] Patent Number: 5,240,686
[45] Date of Patent: Aug. 31, 1993

[54] ARRANGEMENT FOR EMPTYING AND CLEANING HYGIENIC VESSELS

[75] Inventor: Jan Harlegard, Therwil, Switzerland

[73] Assignee: S I C AG, Basle, Switzerland

[21] Appl. No.: 880,288

[22] Filed: May 4, 1992

Related U.S. Application Data

[63] Continuation of Ser. No. 427,012, Dec. 25, 1989, abandoned.

[51] Int. Cl.⁵ .......................... A61L 2/00; B08B 3/00
[52] U.S. Cl. .................................. 422/300; 422/292; 422/302; 422/303; 134/62; 134/152; 134/177; 134/200
[58] Field of Search ............... 422/292, 300, 302, 303; 134/62, 152, 166 R, 177, 200

[56] References Cited

U.S. PATENT DOCUMENTS

| | | | |
|---|---|---|---|
| 1,991,941 | 2/1935 | Jewell | 134/200 |
| 3,645,283 | 2/1972 | Cassells | 134/152 |
| 3,664,355 | 5/1972 | Adams | 134/200 |
| 4,670,061 | 6/1987 | Harlegard | 422/302 |

FOREIGN PATENT DOCUMENTS

| | | |
|---|---|---|
| 0294516 | 12/1988 | European Pat. Off. |
| 500327 | 6/1930 | Fed. Rep. of Germany |
| 3232329 | 1/1984 | Fed. Rep. of Germany |
| 2416007 | 8/1979 | France |
| 1168545 | 10/1969 | United Kingdom |
| 1181133 | 2/1970 | United Kingdom |

OTHER PUBLICATIONS

Harlegard: Translation of first page of EP294516.

Primary Examiner—Michael G. Wityshyn
Assistant Examiner—Timothy J. Reardon
Attorney, Agent, or Firm—Scully, Scott, Murphy & Presser

[57] ABSTRACT

An arrangement for the emptying and cleaning, and when required, for the disinfecting of hygienic vessels which are employed in the health care or nursing sector, without contamination of the external portions of the arrangement. The arrangement for the emptying and cleaning of hygienic vessels, consists of a rinsing chamber with a conical lower portion, with an odor trap, as well as with cleaning nozzles in the rinsing chamber and with a horizontal or vertical trap door.

6 Claims, 4 Drawing Sheets

ARRANGEMENT FOR EMPTYING AND CLEANING HYGIENIC VESSELS

This is a continuation of copending application Ser. No. 427,012 filed on Dec. 25, 1989, now abandoned.

BACKGROUND OF THE INVENTION

1. Field of the Invention

The invention has as an object thereof to develop an arrangement for the emptying and cleaning, and when required, for the disinfecting of hygienic vessels which are employed in the health care or nursing sector, without contamination of the external portions of the arrangement.

This task is of particular significance in the field of hygiene and for the protection against infections encountered in a hospital.

2. Discussion of the Prior Art

From the disclosure of Swiss Patent 602 202 there has become known an arrangement for the rinsing and disinfecting of bedpans, which describes a stand with a rinsing chamber which is connected at the bottom thereof with a discharge and at its upper end possesses an opening which is closable through the intermediary of a horizontally displaceable cover. An annular channel with a discharge gap is provided in a rinsing chamber. A number of spray nozzles are arranged distributed below the annular channel. The annular channel and the spray nozzles are connected with the cold water and hot water pressure line. The interior space of the rinsing chamber is connected with an arrangement for steam condensation, which is located externally of the chamber. The receptacle which is to be cleaned must be introduced by a nurse or health care aide into the rinsing chamber. Thereafter, this person actuates a switch which initiates the programmed control for the activation of the working cycle.

This known arrangement is subject to various disadvantages. When a bedpan containing excrement is to be cleaned, then the nurse must initially tilt the bedpan by hand and empty the bedpan into the rinsing chamber. Thereby, it is almost impossible to prevent the occurrence of a contamination of the exterior and a bacterial infection. This arrangement has also the technical disadvantage of necessitating a large installation space, inasmuch as during opening thereof the cover must be displaced in a horizontal direction.

These disadvantages are avoided through the arrangement constructed pursuant to European Patent 0 093 846. The latter describes an arrangement consisting of a rinsing chamber which, on one side thereof, includes an opening which is closable through a sliding door, and a rotating arrangement which serves for the retention of a hygienic vessel and which is pivotable about a horizontal pivoting axis. The steps for the emptying, cleaning and disinfection are program-controlled.

By means of this known arrangement, subsequent to the emptying of the vessel through operation of the rotating arrangement, through the intermediary of a rotary nozzle which is mounted on the ceiling of the rinsing chamber, there is cleansed the interior space of the rinsing chamber and the outer surfaces of the hygienic vessel which is inserted into the rotary arrangement and thereafter fixedly and exchangeably connected with the rotating arrangement by means of a rotary or swivel coupling; pressurized water being intensively and optimally injected or sprayed by means of nozzle which is located above the center of the hygienic vessel, and the cleaning water being discharged in the lower conical portion of the rinsing chamber. Effected thereafter as a directly following work step is the disinfection of the emptied and cleaned hygienic vessel through the application of steam, after which there is effected the opening for the door with a simultaneous pivoting of the mounting support within the rotating arrangement in a reverse pivoting direction for the withdrawal of the empty, cleaned and disinfected hygienic vessel.

SUMMARY OF THE INVENTION

This arrangement has found widespread acceptance in actual practice. Accordingly, it is now a further object of the present invention to modify and improve upon this arrangement through a constructively simpler embodiment, which does not require any such rotating arrangement with a mounting support in the rinsing chamber.

Furthermore, it is an object of the present invention to increase the throughput capacity through the utilization of 2 urine or secretion flasks.

An object of the arrangement pursuant to the invention is to provide an arrangement for the emptying and cleaning of hygienic vessels, consisting of a rinsing chamber with a conical lower portion, with an odor trap, as well as with cleaning nozzles in the rinsing chamber and with a horizontal or vertical door.

The arrangement of the invention is characterized in that it incorporates a rinsing chamber with a door in which this door is a trapdoor or drop door (5) and which possesses a hinging axis 6 at its lower edge, whereby the drop door possesses in its interior hollow, a piping system (7) with two or more nozzles (9, 9a) arranged on the inside of the door, and with a connected piece (10), and wherein the trapdoor or drop door is upwardly swingable about the hinging axis to be closed, or is closed in a motorized operation, in which the connecting piece is insertable into a connector member (11) which is connected through the piping 12 in the rinsing chamber or through an outwardly conducted pipeline (12) to the piping system (7) of the rinsing chamber (1), in that subsequent to the switching on of the cleaning water, the water jet is directed through the nozzles completely against the underside of the rinsed goods, such as hygienic vessels (8), and when required, upon the application of a cover directs the water jet from one (9a) of the nozzles also against the underside of the cover, in which the cleaning of the rinsed goods on all sides thereof is carried out by means of the cleaning nozzle (17) through the connecting line 16 leading to the cleaning system, or is supported through the further nozzles (4, 4a) in the rinsing chamber, wherein the cleansed and, when required, disinfected vessels can be withdrawn as rinsed goods, when after the completing of the cleaning cycle and shutting off of the water supply, the trapdoor or drop door (5) is opened, and in which the cleaning cycle is repeatable in the same manner.

The arrangement pursuant to the invention is also characterized in that:

this door is a trap door (5) and possesses a hinging axis (6) at its lower edge, whereby the trap or swivel door includes a piping system (7) in its interior hollow with two or more nozzles (9, 9a) arranged on the inside of the door, and with a connecting piece (10), and wherein the trap door is upwardly swingable about the hinging axis so as to close, or closed in a motorized operation, wherein the connecting piece is a flexible hose which is connected through a pipeline in the rinsing chamber or through an outwardly conducted pipeline (12) to the piping system (7) of the rinsing chamber (1), wherein subsequent to the switching in of the cleaning water, the water jet is directed by means of the nozzles completely against the underside of the rinsed goods, such as hygienic vessels (8), and when required upon application of a cover, one of the nozzles (9a) will direct the water jet also against the underside of the cover, and wherein the cleaning of the rinsed goods on all sides thereof through the cleaning nozzle 14 is effected by means of the conduit 12a through the rotating axis to the cleaning system, or is supported through the further nozzles (4, 4a) in the rinsing chamber, that the cleaned and, when required, disinfected vessels can be removed as rinsed goods when, upon completion of the cleaning cycle and the shutting off of the water supply, there is opened the trap or drop door (5), and in which the cleaning sequence is repeatable in the same manner.

The arrangement of the invention is further characterized in that:

this door is a trapdoor or drop door (5), and possesses a hinging axis (6) along its lower edge, whereby the drop door includes a piping system (7) in its interior hollow with two or more nozzles (9, 9a) arranged on the inside of the door, and with a connecting piece (10), and wherein the drop door is swingable upwardly about the hinging axis, or closed in a motorized operating;

wherein the connecting piece is an angle member or elbow which is rotatable about the swivel axis, which is connected through a pipeline arranged in the rinsing chamber or an outwardly conducted pipeline (12) to the piping system (7) of the rinsing chamber (1), wherein subsequent to the switching on of the cleaning water, the water jet is directed by the nozzles completely against the underside of the rinsed goods, such as hygienic vessels (8), and as required upon application of a cover, one of the nozzles (9a) will direct the water jet also against the underside of the cover, wherein the cleaning of the rinsed goods on all sides thereof by the cleaning nozzle (7) is effected by means of the conduit (12a) through the swiveling axis towards the cleaning system, or is supported by the further nozzles (4, 4a) in the rinsing chamber, wherein the cleansed and when required disinfected, vessels can be removed as rinsed goods or items, whereby subsequent to completion of the cleaning cycle and the shutting off of the water supply, the trap door (5) is opened, and the cleaning sequence is repeatable in the same manner.

The arrangement pursuant to the invention is also characterized in that the piping system (7) possesses a nozzle (14) which is arranged on an upwardly and thereafter downwardly bent tube section (15) in such a manner, that a flask (8a) which is to be cleaned, such as a urine or secretion flask, is slid onto the nozzle (14) at a still open trap door (5), and thereby the hygienic vessel (8) and/or the cover and/or one or two flasks, such as urine or secretion flask, are slid into a retaining arrangement, which maintains the goods or item which are to be rinsed in a generally vertical position during the cleaning cycle.

The arrangement of the invention is also characterized through a process for the utilization thereof in that at an opened door (5) of the rinsing chamber (1), inserted into the restraining holder are one or more hygienic vessels (8, 8a) and that these are hereby simultaneously slid over the nozzles (14) at the end of the curved tube (15), and as a result thereof the nozzles are forcibly centered in the necks of the flasks, and thereafter the trapdoor or drop door (5) is swung upwardly closing about the hinge point (6), and thereafter by means of a known program control, cleaning water is injected into the rinsing chamber (1) by means of the piping system (7) through the nozzles (9, 9a, 9b), and through the nozzle (14) which is connected with this piping system (7), there is concurrently injected cleaning water during and after the emptying of the hygienic vessels, and the cleaning of the rinsed goods or items on all sides thereof is effected by means of the cleaning nozzle (17) through the connecting line 16 leading to the cleaning system (7), or supported through the further nozzles (4, 4a) in the rinsing chamber, and the cleaning water and prior thereto the contents of the hygienic vessels are discharged through the conical lower portion (2) and across the odor trap (3), whereby the piping system (7) is inserted into the connectors (11) through the connecting piece 10 upon the closing of the door (5), and by means of the pipelines (12) and (13) the cleaning water is conducted towards the nozzle (17) or (4, 4a) as well as (9, 9a, 9b), and after the completion of the emptying and cleaning, and when required, disinfection, the drop door (5) is swung open, the cleaned hygienic vessels, such as urine and/or secretion flasks, are removed and these process steps are then repeated.

BRIEF DESCRIPTION OF THE DRAWINGS

The arrangement pursuant to the invention is now elucidated on the basis of the accompanying drawing figures.

DETAILED DESCRIPTION

Figure 1:
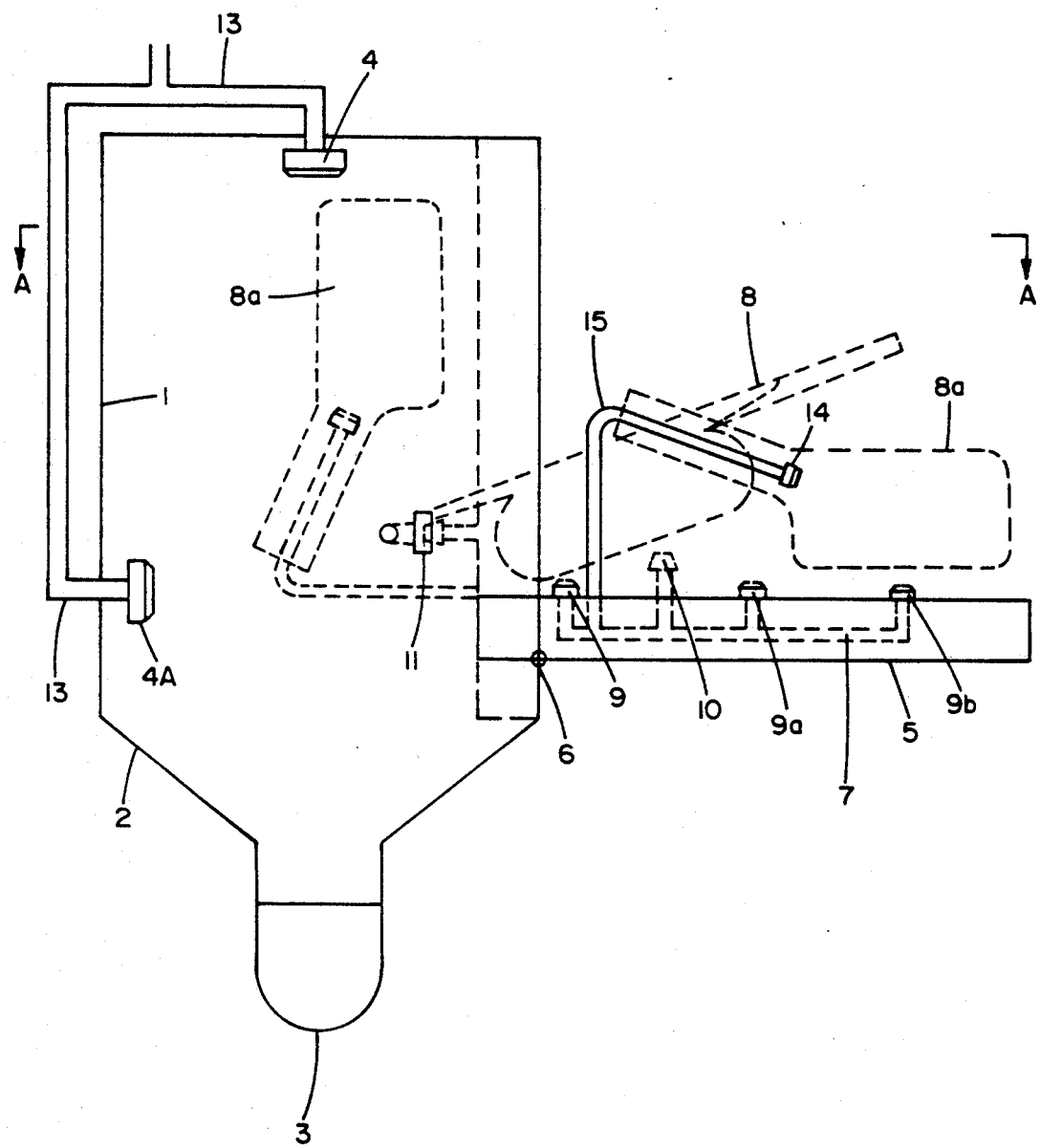
FIG. 1 represents a side view with the door swung open into horizontal position.
Figure 2:
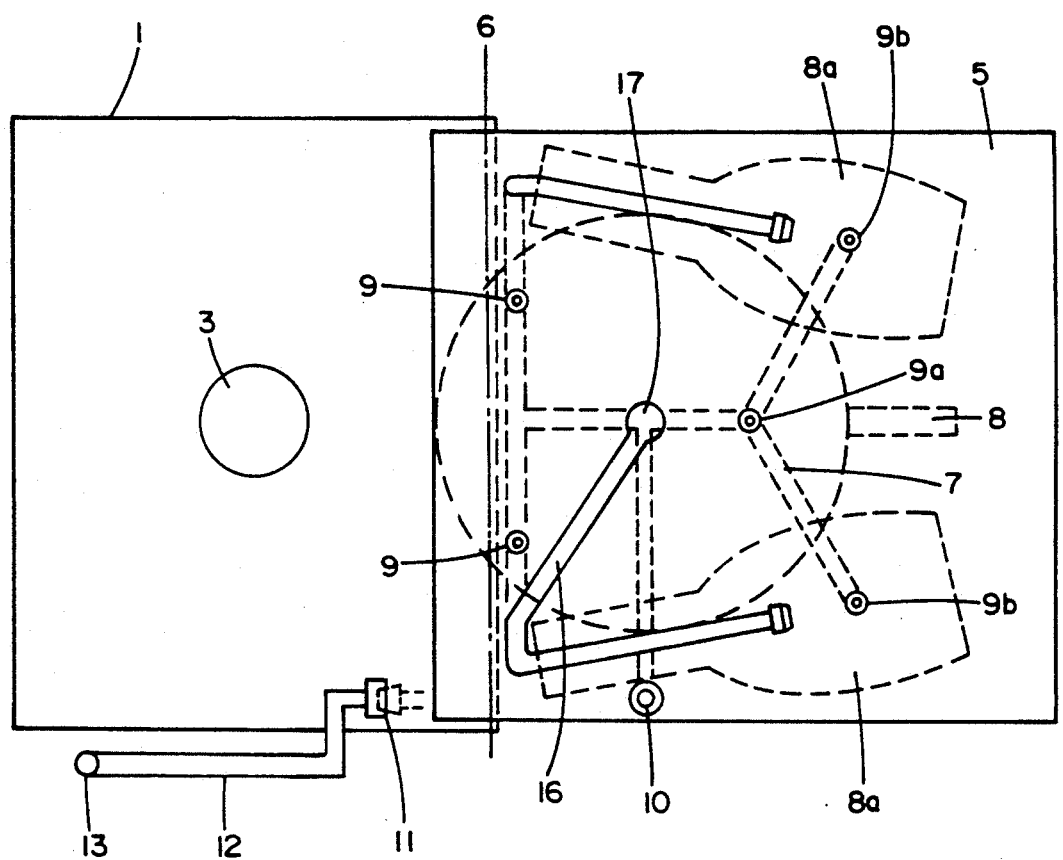
FIG. 2 represents a plan view with the pivoting movement of the hygienic vessel.
Figure 3:
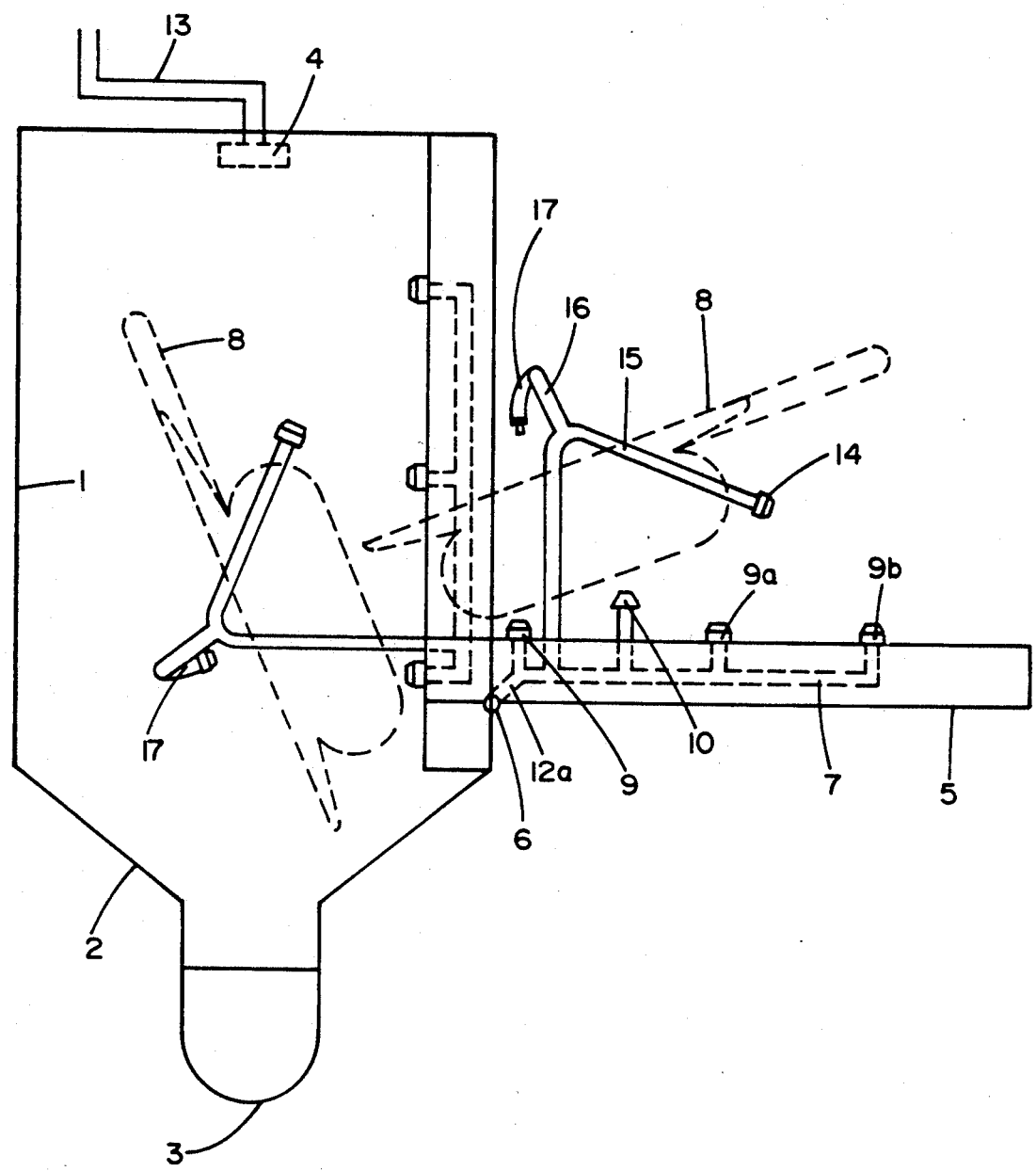
FIG. 3 represents a side view with the pivoting movement of the bedpan.
Figure 4:
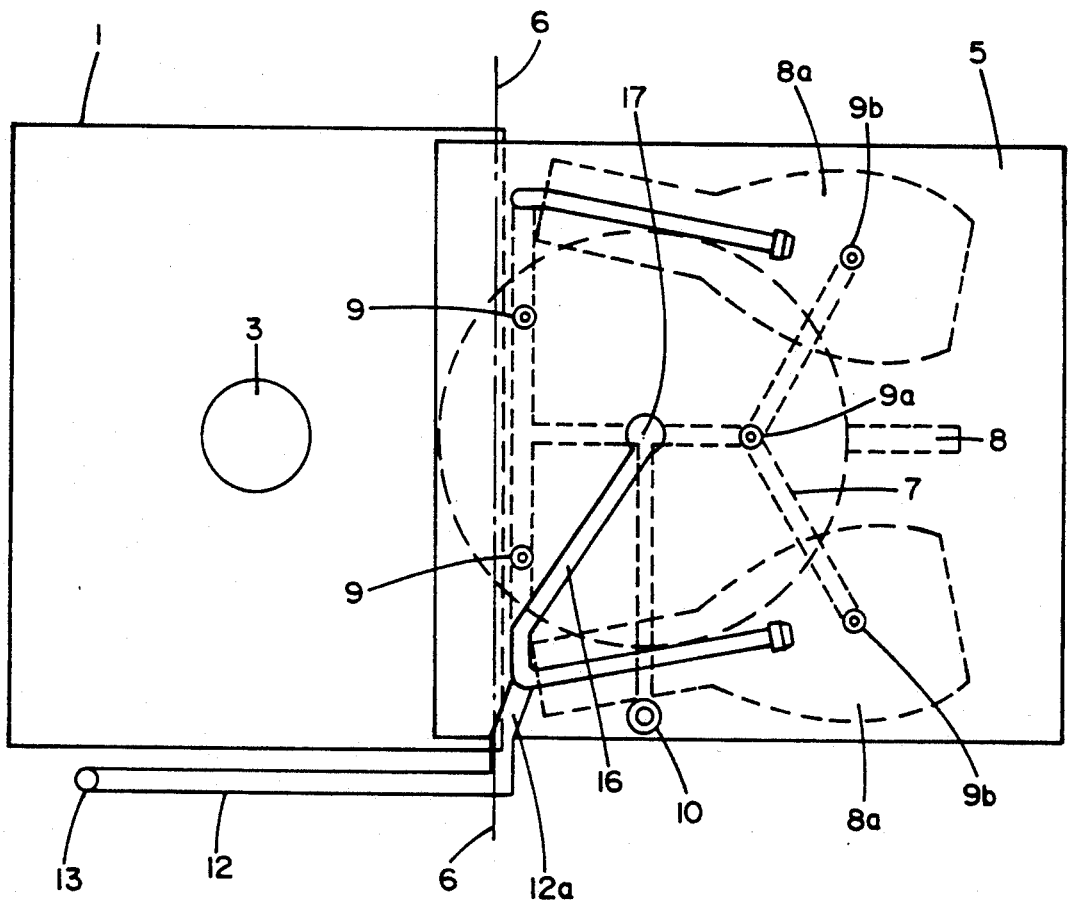
FIG. 4 represents a plan view of the water infeed shown through the pivoting axis for the door.

In the figures the reference numerals identify the following components:

| Numeral | Component |
| --- | --- |
| 1 | Rinsing Chamber |

-continued

| Numeral | Component |
| --- | --- |
| 2 | Conical lower portion |
| 3 | Odor Trap |
| 4, 4a | Cleaning Nozzles |
| 5 | Drop Door |
| 6 | Hinging point |
| 7 | Piping System |
| 8, 8a | Hygienic vessels |
| 9, 9a, 9b | Nozzles |
| 10 | Connecting Piece |
| 11 | Connectors |
| 12, 12a | Pipeline |
| 13 | Pipeline |
| 14 | Nozzle |
| 15 | Curved Pipeline |
| 16 | Connecting Line to the Piping System (7) |
| 17 | Cleaning Nozzle |

In the event that there are employed arrangements with hinged covers, in these the nozzle is arranged within the rinsing chamber. Through this constructive arrangement it is then no longer possible to provide a complete cleaning of all surfaces of the rinsed goods or items. The surface which faces towards the hinged cover remains untouched by the cleaning water.

As a result thereof, it is also no longer possible to effect any assured internal cleaning of the inserted flask. For flasks possessing a narrow flask neck, upon closing of the door, the nozzle remains outside of the opening of the flask. At a larger opening, the nozzle is inserted therein without being centered. The cleaning of the flask becomes thereby uncertain and incomplete.

These disadvantages are avoided by the arrangement pursuant to the invention. This completely cleans the goods or items being rinsed on all sides and, namely, the external and internal surfaces within an optimally short period of time.

The arrangement pursuant to the invention is also characterized by a preferred process for its utilization. This process is characterized in that, with a swung open door (5) for the rinsing chamber (1), there are inserted into the restraining holder one or more hygienic vessels (8, 8a) and these are thereby simultaneously slid over the nozzles (14) at the end of the curved pipe or tube (15), and as a result the nozzles are forcibly centered within the flask necks, thereafter the drop door (5) is closed by being swung upwardly about the hinging point (6), and subsequently through a known program control, through the intermediary of the piping system (7), cleaning water is injected through the nozzles (9, 9a, 9b) into the rinsing chamber (1), and by means of the nozzle (14) which is connected to this piping system (7) there is concurrently injected cleaning water during and subsequent to the emptying of the hygienic vessels, and the cleaning of the rinsed goods or items on all sides thereof through the cleaning nozzles (17) which are connected by the connecting line (16) with the cleaning system (7), or through the line (12a) and through the swiveling point (6) with the cleaning system (7), or is supported by means of the further nozzles (4, 4a) in the rinsing chamber, and wherein the cleaning water and previously thereto the contents of the hygienic vessels are discharged through the conical lower portion (2) and across the odor trap (3), whereby the piping system 7 is introduced into the connectors (11) through the connecting piece (10) upon the closing of the door (5), and by means of the pipelines 12 and 13 the cleaning water is conducted towards the nozzle (17) or (4, 4a), as well as (9, 9a, 9b), and after completion of the emptying and cleaning, and when required, disinfection, the drop door (5) is swung open, the cleaned hygienic vessels, such as urine and/or secretion flasks, are removed and these process steps are then repeated.

The process pursuant to the invention, employs bedpans instead of the hygienic vessels in the shape or urine or secretion flasks, which are inserted into another restraining holder.

The process of the invention utilizes, as required, such a tube (15) with nozzle (14) which sprays into the inside of the bedpan in addition to the nozzle (4a), and thereby securely removes any kind of more adherent accretions.

The arrangement pursuant to the invention, in conjunction with the process for the implementation thereof, is hereby elucidated through the following illustrative example:

A nurse or healthcare aide, by means of applying elbow-pressure to a pushbutton, opens through a motorized operation the drop door (5) and places two filled urine flasks into the restraining holder, and which are hereby concurrently slid over the nozzles (14) at the end of the curved tube (15) and are thereby centered. Thereafter, through exerting further pressure on a pushbutton, the drop door (5) is closed in a motorized operation and, due to the motorized pivoting of the drop door (5) the connecting piece (10) is pressed into the connectors (11), thereafter through the utilization of a programmed control, cleaning water is injected through the pipings (7, 13) towards the nozzles (4, 4a, 9, 9a, 9b) and into the rinsing chamber (1), and sprayed into the urine flasks through the nozzle (14), inasmuch as due to the pivoting of the drop door (5), any urine liquid in the conical lower portion (2) has already been discharged and across the odor trap (3), and wherein the cleaning water will also similarly discharge thereby.

The cleaning and rinsing time period consists of 25 seconds and, if required, this can be extended through changing of the time setting.

Implemented thereafter is a disinfection by means of steam with an additionally installed arrangement and pursuant to the process described in European Patent 0 093 846 through the intermediary of the process control. Thereafter, through application of a pushbutton pressure, the drop door (5) is opened in a motorized operation, and the emptied and cleaned, as well as additionally disinfected, urine flasks are removed.

The entire cycle from insertion up to the removal of the urine flasks, without disinfection, requires 40 seconds, and with the alternative incorporation of disinfection, requires 240 seconds.

The arrangement pursuant to the invention, together with the process for the implementation thereof, affords the advantage of an assured cleaning of the inserted goods or items to be rinsed on all sides thereof, such as flasks or bedpans, within a short period of time. This advantage also consists of in that a complete internal and external cleaning of the inserted flasks or bedpans is effectuated within a short period of time with the usage of an optimum quantity of water. For the cleaning cycle there is necessitated the use of only about 25 liters of water. Hereby, the technical advantage also resides in that the constructive assembly of the arrangement pursuant to the invention does not require any rotating arrangement with actuating mechanism and control. The constructive assembly of the arrangement pursuant to the invention is simpler, and thereby requires only lower investment costs. A further advantage consists of in that, by means of the restraining holder, a plurality of flasks, especially two flasks, can be simultaneously inserted, and thereby the throughput capacity allows itself to be increased.

What is claimed is:

1. In an apparatus for the emptying and cleaning of hygienic vessels, said apparatus comprising a rinsing chamber (1) having a conical lower portion (2), an odor trap (3) connected to a lower end of said conical lower portion, a first set of cleaning nozzles (4, 4a) supplied with cleaning water from a pipeline (13) outwardly conducted from said rinsing chamber, and a vertical closure door (5) for said rinsing chamber having a hinging axle (6) along a lower edge of said closure door (5);

the improvement comprising: said closure door (5) having an interior hollow space, a piping system (7) and a connecting line (12a) being arranged in said hollow space of said door (5), said connecting line (12a) connected to said piping system (7), a rotatable angle piece (10) located centrally on the housing axle (6) and being connected to said connecting line (12a), a second set of nozzles (9, 9a, 9b) protruding from an inner side of said door (5) into said rinsing chamber (1), said second set of nozzles being operatively connected with said piping system (7), a pipe conduit (12) outwardly conducted from said rinsing chamber for conducting cleaning water into said chamber such that upon the closing of said closure door said angle piece (10) operatively connects with said pipe conduit (12) so that cleaning water will flow from said pipe conduit through said second set of nozzles;

a first angled conduit (15) connected with said piping system (7), said first angled conduit protruding from said inner side of said door into said chamber and directed towards said inner side of said door, said first angled conduit including a third nozzle (14) for central insertion into the neck of a urine flask for the internal cleaning of said flask, said first angled conduit including a second angled conduit (16) branching off from said first angled conduit (15) in the angled region thereof and including a fourth rinsing chamber cleaning nozzle (17) for the concurrent external cleaning of said urine flask inserted into said rinsing chamber, said first angled conduit also being adapted to clean the exterior of an hygienic vessel inserted so that said second angled conduit cleans the interior of said hygienic vessel.

2. In an apparatus for the emptying and cleaning of hygienic vessels, said apparatus comprising a rinsing chamber (1) having a conical lower portion (2), an odor trap (3) connected to a lower end of said conical lower portion, a first set of cleaning nozzles (4, 4a) supplied with cleaning water from a pipeline (13) outwardly conducted from said rinsing chamber, and a vertical closure door (5) for said rinsing chamber having a hinging axle (6) along a lower edge of said closure door (5);

the improvement comprising: a pipe conduit outwardly conducted from said rinsing chamber for conducting cleaning water through a connector (11) into said rinsing chamber, a connecting member (10) engaging into a piping system (7) located in a hollow space of said door (5) for conducting water to said piping system from said connector (11), a second set of nozzles (9, 9a, 9b) receiving water from said piping system (7), said second set of nozzles protruding from an inner side of said door (5) into said rinsing chamber (1);

a first angled conduit (15) connected with said piping system (7), said first angled conduit protruding from said inner side of said door into said chamber and directed towards said inner side of said door, said first angled conduit including a third nozzle (14) for central insertion into the neck of a urine flask for the internal cleaning of said flask, said first angled conduit including a second angled conduit (16) branching off from said first angled conduit (15) in the angled region thereof and including a fourth rinsing chamber cleaning nozzle (17) for the concurrent external cleaning of said urine flask inserted into said rinsing chamber, said first angled conduit also being adapted to clean the exterior of an hygienic vessel inserted so that said second angled conduit cleans the interior of said hygienic vessel.

3. The apparatus of claim 1, wherein said closure door (5) is manually pivotable about said hinging axle (6).

4. The apparatus of claim 1, wherein said closure door (5) includes means for the motorized pivoting thereof about said hinging axle (6).

5. The apparatus of claim 2, wherein said closure door (5) is manually pivotable about said hinging axle (6).

6. The apparatus of claim 2, wherein said closure (5) includes means for the motorized pivoting thereof about said hinging axle (6).

* * * * *

UNITED STATES PATENT AND TRADEMARK OFFICE
CERTIFICATE OF CORRECTION

PATENT NO.  : 5,240,686
DATED       : August 31, 1993
INVENTOR(S) : Jan Harlegard It is certified that error appears in the above-indentified patent and that said Letters Patent is hereby corrected as shown below:

On the Title Page, Section [73]: "Basle" should read --Basel--

On the Title Page, Section [63]: "Dec. 25," should read --Oct. 25,--

Column 1, line 6: "Dec. 25," should read --Oct. 25,--

Column 7, lines 21-22: "housing" should read --hinging--

Signed and Sealed this

Thirtieth Day of August, 1994

Attest:

BRUCE LEHMAN

*Attesting Officer*     *Commissioner of Patents and Trademarks*